(12) United States Patent
Yao et al.

(10) Patent No.: US 10,702,500 B2
(45) Date of Patent: *Jul. 7, 2020

(54) METHODS OF TREATING CANCER

(71) Applicant: Macau University of Science and Technology, Macau (CN)

(72) Inventors: Xiao Jun Yao, Macau (CN); Lai Han Elaine Leung, Macau (CN); Liang Liu, Macau (CN); Qian Qian Wang, Macau (CN); Jia Hui Xu, Macau (CN); Ying Li, Macau (CN)

(73) Assignee: MACAU UNIVERSITY OF SCIENCE AND TECHNOLOGY, Macau (CN)

( * ) Notice: Subject to any disclaimer, the term of this patent is extended or adjusted under 35 U.S.C. 154(b) by 57 days.

This patent is subject to a terminal disclaimer.

(21) Appl. No.: 16/257,018

(22) Filed: Jan. 24, 2019

(65) Prior Publication Data

US 2019/0175553 A1 Jun. 13, 2019

Related U.S. Application Data

(63) Continuation of application No. 15/839,875, filed on Dec. 13, 2017, now Pat. No. 10,278,955.

(51) Int. Cl.
*A61K 31/4045* (2006.01)
*A61K 45/06* (2006.01)
*G01N 33/574* (2006.01)
*A61P 35/00* (2006.01)
*C12Q 1/48* (2006.01)

(52) U.S. Cl.
CPC .......... *A61K 31/4045* (2013.01); *A61K 45/06* (2013.01); *A61P 35/00* (2018.01); *C12Q 1/48* (2013.01); *G01N 33/57423* (2013.01); *G01N 33/57496* (2013.01); *G01N 2333/91017* (2013.01)

(58) Field of Classification Search
None
See application file for complete search history.

(56) References Cited

PUBLICATIONS

Hamamoto, R., et al. (2016). Dysregulation of protein methyltransferases in human cancer: An emerging target class for anticancer therapy. Cancer Science, 107(4), 377-384.

Stopa, N., et al. (2015). The PRMT5 arginine methyltransferase: many roles in development, cancer and beyond. Cellular and Molecular Life Sciences.
Shimizu, D., et al. (2016). The protein arginine methyltransferase 5 promotes malignant phenotype of hepatocellular carcinoma cells and is associated with adverse patient outcomes after curative hepatectomy. International Journal of Oncology, 50, 381-386.
Kryukov, G. V., et al. (2016). MTAP deletion confers enhanced dependency on the PRMT5 arginine methyltransferase in cancer cells. Science.
Ibrahim, R., et al. (2014). Expression of PRMT5 in lung adenocarcinoma and its significance in epithelial-mesenchymal transition. Human Pathology.
Zhang, B., et al. (2015). Targeting protein arginine methyltransferase 5 inhibits human hepatocellular carcinoma growth via the downregulation of beta-catenin. Journal of Translational Medicine, 13, 1-10.
Sheng, X., et al. (2016). Protein arginine methyltransferase 5 regulates multiple signaling pathways to promote lung cancer cell proliferation. BMC cancer, 16, 1-13.
Chan-Penebre, E., et al. (2015). A selective inhibitor of PRMT5 with in vivo and in vitro potency in MCL models. Nature chemical biology, 11, 432-441.
Di Lorenzo, A., et al. (2011). Histone Arginine Methylation. FEBS letters, 585(13), 1-16.
Zhang, B., et al. (2015). Targeting protein arginine methyltransferase 5 inhibits colorectal cancer growth by decreasing arginine methylation of eIF4E and FGFR3. Oncotarget, 6(26), 22799-22811.
Scoumanne, A., et al. (2009). PRMT5 is required for cell-cycle progression and p53 tumor suppressor function. Nucleic Acids Research, 37(15), 4965-4976.
Wendel, H. G., et al. (2004). Survival signaling by Akt and eIF4E in oncogenesis and cancer therapy. Nature, 428, 332-337.
Kang, S., et al. (2007). FGFR3 Activates RSK2 to Mediate Flematopoietic Transformation through Tyrosine Phosphorylation of RSK2 and Activation of the MEK/ERK Pathway. Cancer Cell, 12, 201-214.

*Primary Examiner* — Dennis Heyer
(74) *Attorney, Agent, or Firm* — Eagle IP Limited; Jacqueline C. Lui

(57) ABSTRACT

One embodiment is a method of treating cancer. The method includes administering a therapeutically effective amount of a compound to a patient. The compound is represented by Formula I:

Formula I

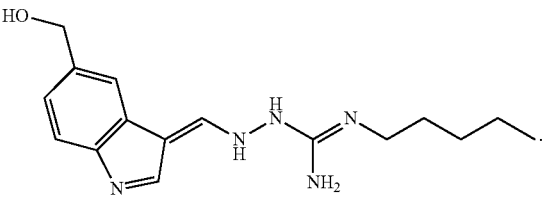

7 Claims, 12 Drawing Sheets
(6 of 12 Drawing Sheet(s) Filed in Color)

| Cell lines | IC$_{50}$ (μM) |
|---|---|
| A549 | 5.80±1.00 |
| H460 | 5.33±1.48 |

METHODS OF TREATING CANCER

FIELD OF THE INVENTION

The present invention relates to a method of treating cancer. The present invention also relates to inhibitors that target the mammalian protein arginine methyltransferases (PRMTs).

BACKGROUND

Cancer is the most common cause of death all over the world. In addition to genetic changes of driver genes in cancer, epigenetic alterations such as changes in DNA methylation, histone modifications, and chromatin organization impact gene expression and cellular gene function, and play an important role in the onset and progression of cancer.

In view of the demand for treating cancer in a patient, more methods and compositions that effectively treat cancer are desired.

SUMMARY

One example embodiment is a method of treating cancer in a patient. The method includes administering to the patient a therapeutically effective amount of a compound of Formula I as follows:

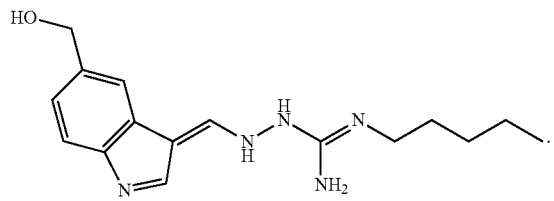

Formula I

Other example embodiments are discussed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1C shows IC50 values of compound T1551 in A549 cells and H460 cells in accordance with an example embodiment.

DETAILED DESCRIPTION

Figure 1A:
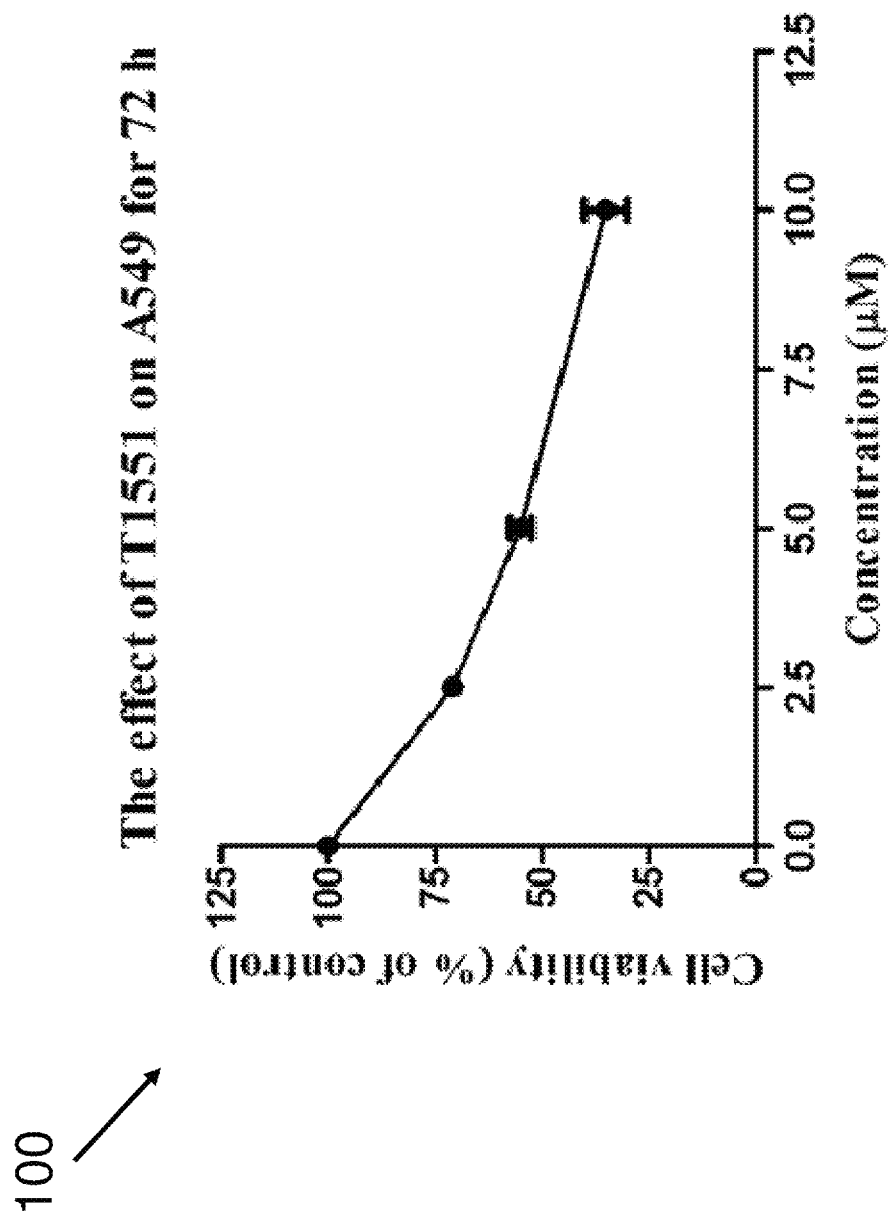
FIG. 1A shows the effect of compound T1551 on the cell viability of A549 cells for 72 hr treatment by MTT assay in accordance with an example embodiment.

Example embodiments relate to methods of treating cancer. The methods include administering a therapeutically effective amount of a compound to a patient. The compound is represented by Formula I:

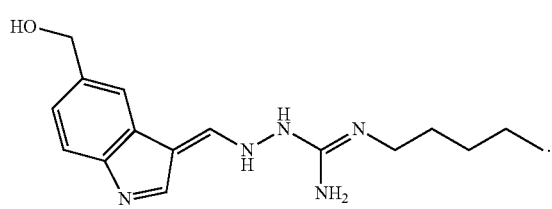

Formula I

In one example embodiment, the cancer is associated with overexpression or high expression of protein arginine methyltransferase 5 (PRMT5).

PRMT belong to a class of nine enzymes that perform NG-mono methylation, asymmetric-, or symmetric-dimethylation of arginine residues on a range of nuclear and cytoplasmic protein substrates. PRMTs can be divided into three subclasses, i.e. types I, II and III. PRMT5 as type II PRMTs, is responsible for catalyzing the symmetrical dimethylation of arginine residues within target proteins. PRMT5 is involved in diverse cellular and biological processes including transcriptional regulation, RNA metabolism and ribosome biogenesis. For example, PRMT5-driven methylation of arginine residues leads to symmetric dimethylation of histone H4 (H4R3me2s), which in turn alters chromatin structure to promote transcriptional repression.

PRMT5 plays a key role in the tumorigenesis, and is upregulated in lymphomas, breast cancer, lung cancer, colorectal cancer and glioblastoma. A high cytoplasmic expression of PRMT5 is closely related to the high-grade subtypes of primary lung adenocarcinomas and a poor prognosis. PRMT5 can regulate multiple signaling pathways to promote lung cancer cell proliferation. Therefore, PRMT5 inhibitors are therapeutic agents for treating cancer.

An example embodiment provides a method to target PRMT5 mediated tumorigenesis in cancers with compound T1551 (i.e. compound of Formula I). Compound T1551 with indole scaffold inhibits PRMT5 methyltransferase activity. T1551 can decrease cell viability of A549 and H460 cells, reduce symmetric dimethylation level of H4R3, downregulate protein expression of two target genes of PRMT5, i.e. FGFR3 and eIF4E, and inhibit the activation of PI3K/AKT/mTOR and ERK signaling.

An example embodiment provides a method of treating cancer in a patient by administering compound T1551 to the patient. In one example embodiment, tumor cells of the cancer express a higher level of PRMT5 than normal cells express. In one example embodiment, tumor cells of the cancer express a higher level of PRMT5 than healthy cells express. In one example embodiment, the cancer is selected from a group consisting of lymphomas, breast cancer, lung cancer, colorectal cancer, myeloma, ovarian cancer, and glioblastoma. In one example embodiment, the cancer is non-small cell lung cancer.

In one example embodiment, compound T1551 is administered in combination with one or more additional PRMT5 inhibitors to the patient.

In one example embodiment, a patient is diagnosed as the patient with the cancer by determining an expression level of PRMT5. If the expression level of PRMT5 is higher than that of normal or healthy cells or tissues, the patient is diagnosed as the cancer that can be treated by compound T1551.

An example embodiment provides a method of treating a disease associated with overexpression of PRMT5. The disease associated with overexpression of PRMT5 relates to PRMT5-driven methylation of arginine residues which leads to symmetric dimethylation of histone H4 (H4R3me2s). Compound T1551 inhibits PRMT5-driven methylation of arginine residues and thereby ameliorate the progress of the disease associated with overexpression of PRMT5.

In one example embodiment, the disease associated with overexpression of PRMT5 includes but not limited to cancer and inflammation.

An example embodiment provides a pharmaceutical composition that includes compound T1551.

In one example embodiment, the pharmaceutical composition is used to treat cancer. In one example embodiment, tumor cells of the cancer express a higher level of PRMT5 than normal cells do. In one example embodiment, the cancer is selected from a group consisting of lymphomas, breast cancer, lung cancer, colorectal cancer, myeloma, ovarian cancer, and glioblastoma. In one example embodiment, the cancer is non-small cell lung cancer. In one example embodiment, the pharmaceutical composition is used to treat a disease associated with overexpression of PRMT5.

In one example embodiment, the pharmaceutical composition includes one or more additional PRMT5 inhibitors. In one example embodiment, the pharmaceutical composition includes a pharmaceutically acceptable excipient or carrier. The pharmaceutically acceptable excipient or carrier includes but not limited to fillers (diluents), binders, disintegrating agents, lubricants, and glidants.

In one example embodiment, the pharmaceutical compositions can be administered by various routes, e.g., oral, subcutaneous, transdermal, intramuscular, intravenous, or intraperitoneal. Routes of administering the pharmaceutical composition include systematic delivery or local delivery to an organ or tissue.

Example 1 Material and Methods

1. MTT Assay

Compound T1551 was purchased from Topscience company (Shanghai, China), dissolved in DMSO and stored at −40° C. A549 and H460 cells were obtained from American Type Culture Collection and cultured in environment of 5% $CO_2$ at 37° C. in RPMI-1640 medium supplemented with 10% FBS, 100 units/mL penicillin and 100 μg/mL streptomycin. Cells were cultured in 96-cell plates at a density of 3,000 cells/well overnight for cell adhesion. With the treatment with DMSO or various concentrations of compound T1551 for 72 hr, each well was added 10 μL MTT (5 mg/mL) and incubated for 4 hr at 3° C., followed by adding 100 μL acidic isopropanol (10% SDS and 0.01 mol/L HCl). Finally, optical density (OD) of each well was measured at 570 nm by Microplate Reader (Tecan, Morrisville, N.C., USA).

2. PRMT5 Methyltransferase Activity Assay PRMT5 enzymatic assay was carried out by Shanghai Chem Partner Co. (998 Halei Road, Pudong New Area, Shanghai, 201203, China). 10 concentrations of compound T1551 were tested to measure the IC50 values. T1551 was prepared as 10 mM stock in DMSO and diluted to final concentration in DMSO. PRMT5 and substrates were incubated with indicated concentrations of compounds in a 384-well plate for 60 min at room temperature. Then, acceptor and donor solutions were added to label the residual substrates of PRMT5. The labeling process was lasting for 60 min at room temperature, followed by reading endpoint with EnSpire with Alpha mode.

3. Western Blot Analysis

A549 and H460 cells were rinsed with PBS and lysed in RIPA lysis buffer supplemented with a protease and phosphatase inhibitors (Thermo Scientific 78440, USA) for 30 min. Cell lysates were centrifuged for 10 min (12,000 g, 4° C.). The supernatant was collected, and protein concentration was calculated with a Bio-Rad DC™ protein assay kit (Bio-Rad, Philadelphia, Pa., USA). 50 μg protein lysate were separated by 10% SDS-polyacrylamide gel electrophoresis and transferred to a nitrocellulose (NC) membrane. Then, membranes were incubated with primary antibody (1:1000), and with a fluorescence-conjugated secondary antibody (1:10000). GAPDH was used as the loading control for normalization. The signal of membranes was scanned with a LI-COR Odyssey Scanner (Belfast, Me., USA).

4. Molecular Docking

Molecular docking calculation was performed with Schrodinger software (Schrodinger, Inc., New York, N.Y., 2015). Crystal complex of PRMT5, SAM and EPZ015666 was derived from RCSB protein data bank (PDBID: 4X61). After the preparation for protein with Prep Wiz in Maestro, a grid file was generated based on the position of EPZ015666 for docking. Compound T1551 was then preprocessed by LigPrep under OPLS-2005 force field, and the low-energy three dimensional conformers were created. Finally, Glide with the standard precision (SP) mode was used to dock compound T1551 into PRMT5 binding pocket. The pose with the lowest docking score was chosen for further binding mode analysis.

5. Statistical Analysis

Statistical analysis was conducted using Graph Prim5.0 software. Descriptive analytical data were presented as means±SEM. Multiple comparisons were evaluated by one-way analysis of variance (ANOVA) method. $P<0.05$ were considered statistically significant.

Example 2 Effect of Compound T1551 in Decreasing Cell Viability of NSCLC Cells

Figure 1B:
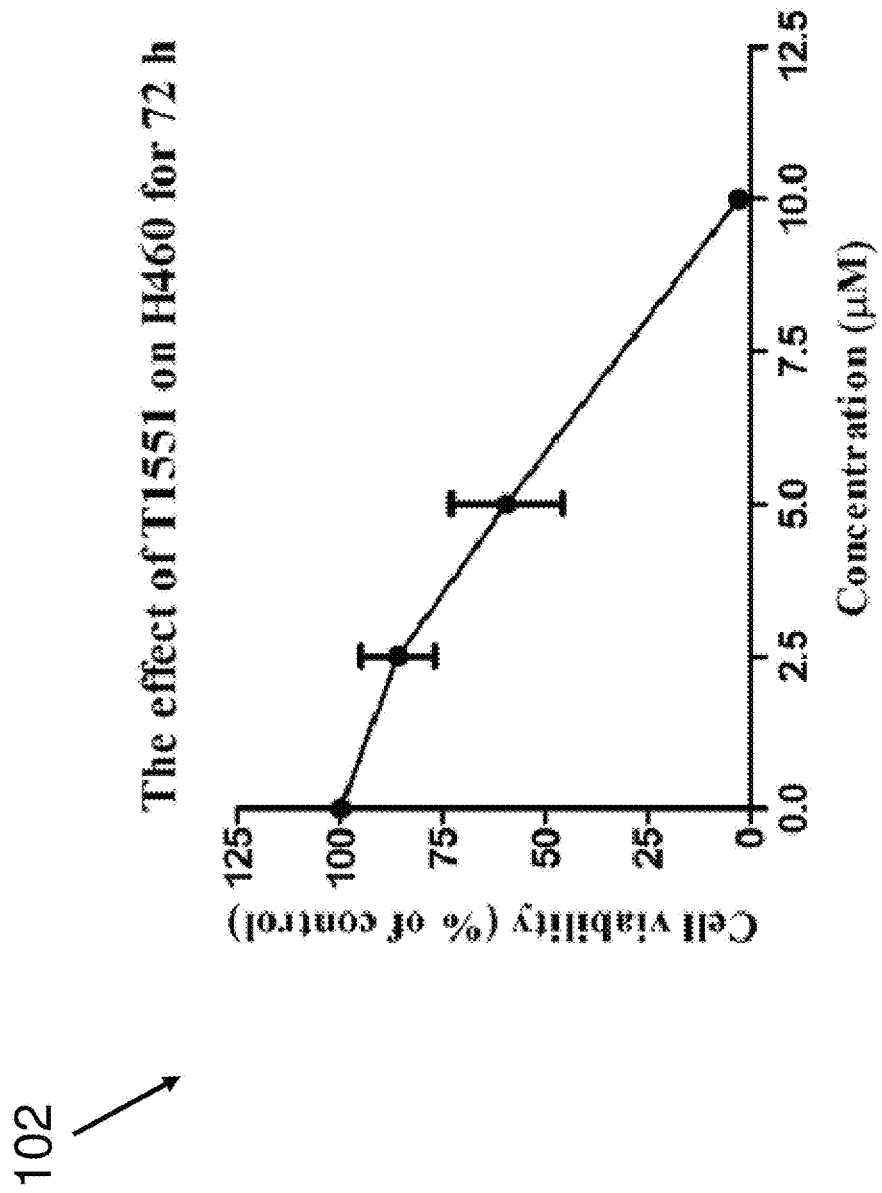
FIG. 1B shows the effect of compound T1551 on the cell viability of H460 cells for 72 hr treatment by MTT assay in accordance with an example embodiment.

FIG. 1A is a graph 100 showing the effect of compound T1551 on the cell viability of A549 cells. FIG. 1B is a graph 102 showing the effect of compound T1551 on the cell viability of H460 cells.

MTT assay was used to evaluate the cytotoxicity of compound T1551 in NSCLC cell lines, A549 and H460.

A549 and H460 cells were incubated with a range of compound T1551 concentrations (i.e. 0, 2.5, 5.0 and 10.0 μM) for 72 hr. As shown in FIGS. 1A and 1B, compound T1551 significantly decreased cell viability in A549 cells and H460 cells in a concentration-dependent manner.

FIG. 1C is a table 104 showing the IC50 values of compound T1551 in A549 and H460 cells. The IC50 values are 5.80±1.00 μM for A549 cells and 5.33±1.48 μM for H460 cells, respectively.

Example 3 Inhibition of Compound T1551 on PRMT5 Methyltransferase Activity

Figure 2:
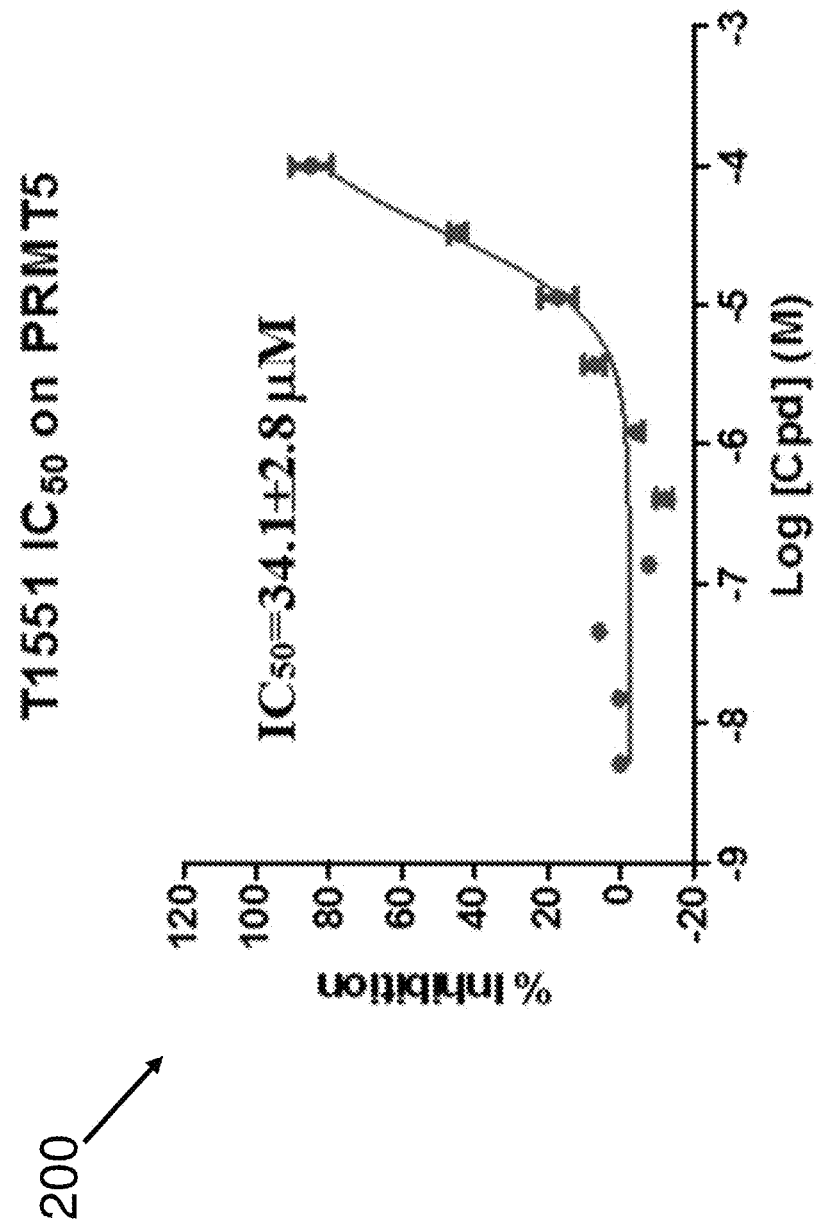
FIG. 2 shows the inhibition of compound T1551 on PRMT5 methyltransferase activity in accordance with an example embodiment.

FIG. 2 is a graph 200 showing the inhibition of compound T1551 on PRMT5. AlphaLISA assay was carried out to investigate the effect of compound T1551 on enzymatic activity of PRMT5. FIG. 2 showed that compound T1551 inhibited PRMT5 enzyme activity in a concentration-dependent manner. The corresponding IC50 value was 34.1±2.8 μM, indicating that compound T1551 could directly inhibit the methyltransferase function of PRMT5.

Example 4 Effect of Compound T1551 in Decreasing the Symmetric Dimethylation Level of Histone 4

Figure 3:
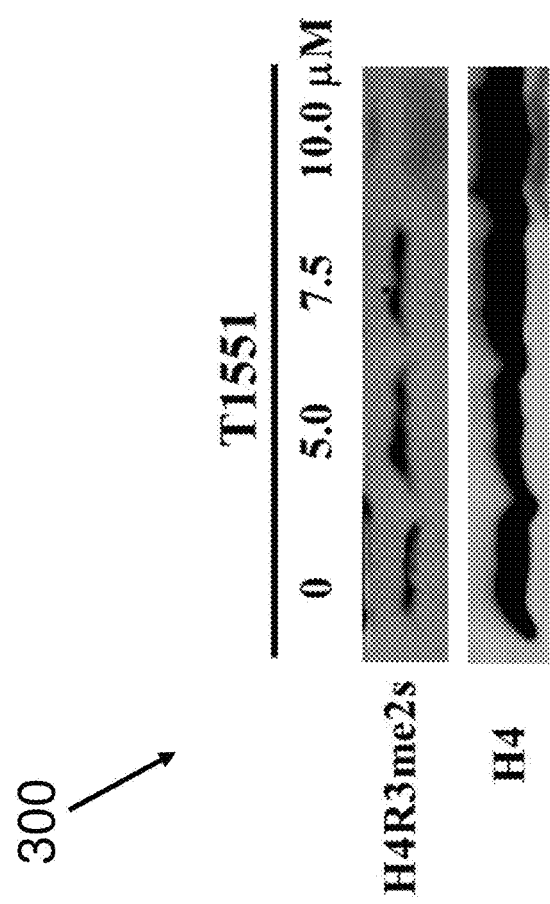
FIG. 3 shows the western blot analysis for H4R3me2s expression in A549 cells treated with compound T1551 for 24 hr in accordance with an example embodiment.

FIG. 3 shows the western blot analysis 300 for histone 4 (H4) and H4R3me2s in A549 cells treated by compound T1551.

Since PRMT5-driven methylation of arginine residues can lead to symmetric dimethylation of arginine residue 3 of histone 4, the expression level of H4R3me2s protein in A549 cells treated with and without compound T1551 was analyzed to investigate the effect of compound T1551 on PRMT5 catalytic substrate. A549 cells were treated by different concentrations of compound T1551, i.e. 0, 5, 7.5 and 10 μM. The total H4 was used as loading control. As shown in FIG. 3, after treating the cells with T1551 for 24 hr, the global level of H4R3me2s is notably decreased. Therefore, from the perspective of histone substrate, it proves that compound T1551 can inhibit PRMT5 methyltransferase activity.

Figure 4:
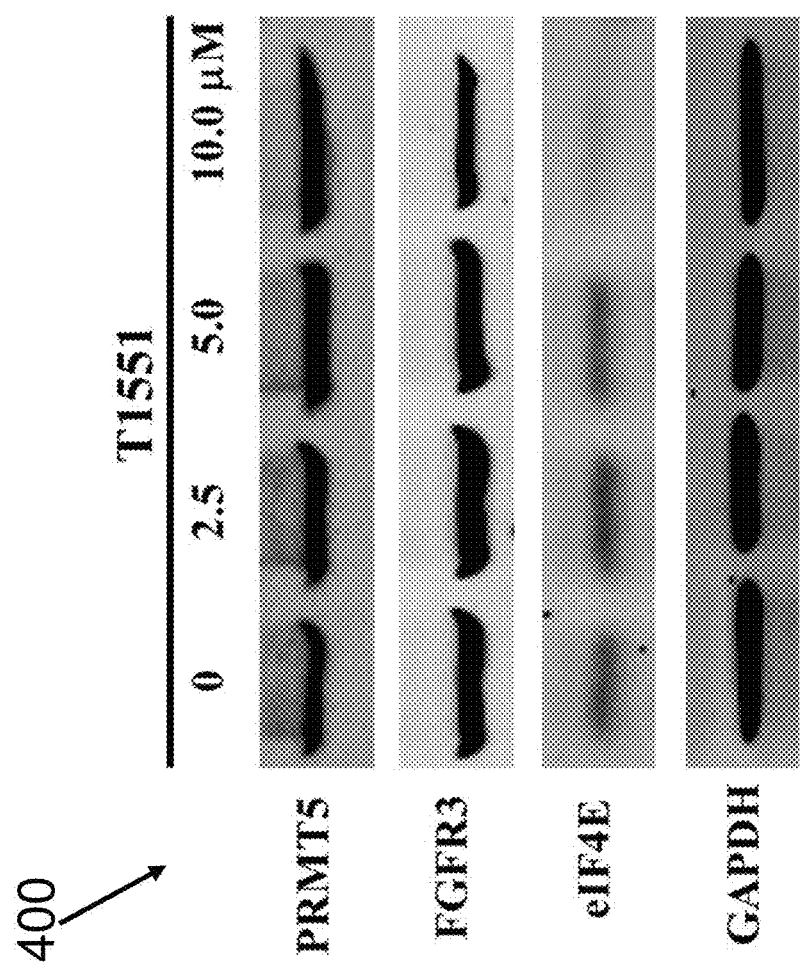
FIG. 4 shows the western blot analysis for the expression of oncogene FGFR3 and eIF4E in A549 cells treated with compound T1551 for 24 hr in accordance with an example embodiment.

Example 5 Effect of Compound T1551 on the Down-Regulation of the Expression of PRMT5 Target Genes FIG. 4 shows the western blot analysis 400 for the expression of target genes, i.e. FGFR3 and eIF4E.

PRMT5 exerts its function by regulating the expression of target genes, such as oncogene FGFR3 and eIF4E. FGFR3 and eIF4E were previously reported to frequently overexpress in cancer including lung cancer, myeloma and ovarian cancers, and thus the expression of FGFR3 and eIF4E plays an important role in tumor occurrence and development. The FGFR signaling has been targeted to treat cancer such as lung cancer. Using RNA interference technology, PRMT5 knockdown could down-regulate FGFR3 and eIF4E expression.

The protein expression levels of these two target genes FGFR3 and eIF4E in A549 cells treated with different concentrations of compound T1551 (i.e. 0, 2.5, 5, and 10 μM) were analyzed to evaluate the relationship of PRMT5, compound T1551 and FGFR3/eIF4E. GAPDH was used as the loading control. As shown in FIG. 4, FGFR3 and eIF4E expression significantly decreased in A549 cells treated with 10 μM of compound T1551. It shows that compound T1551 can reduce FGFR3 and eIF4E expression by inhibiting PRMT5.

Figure 5:
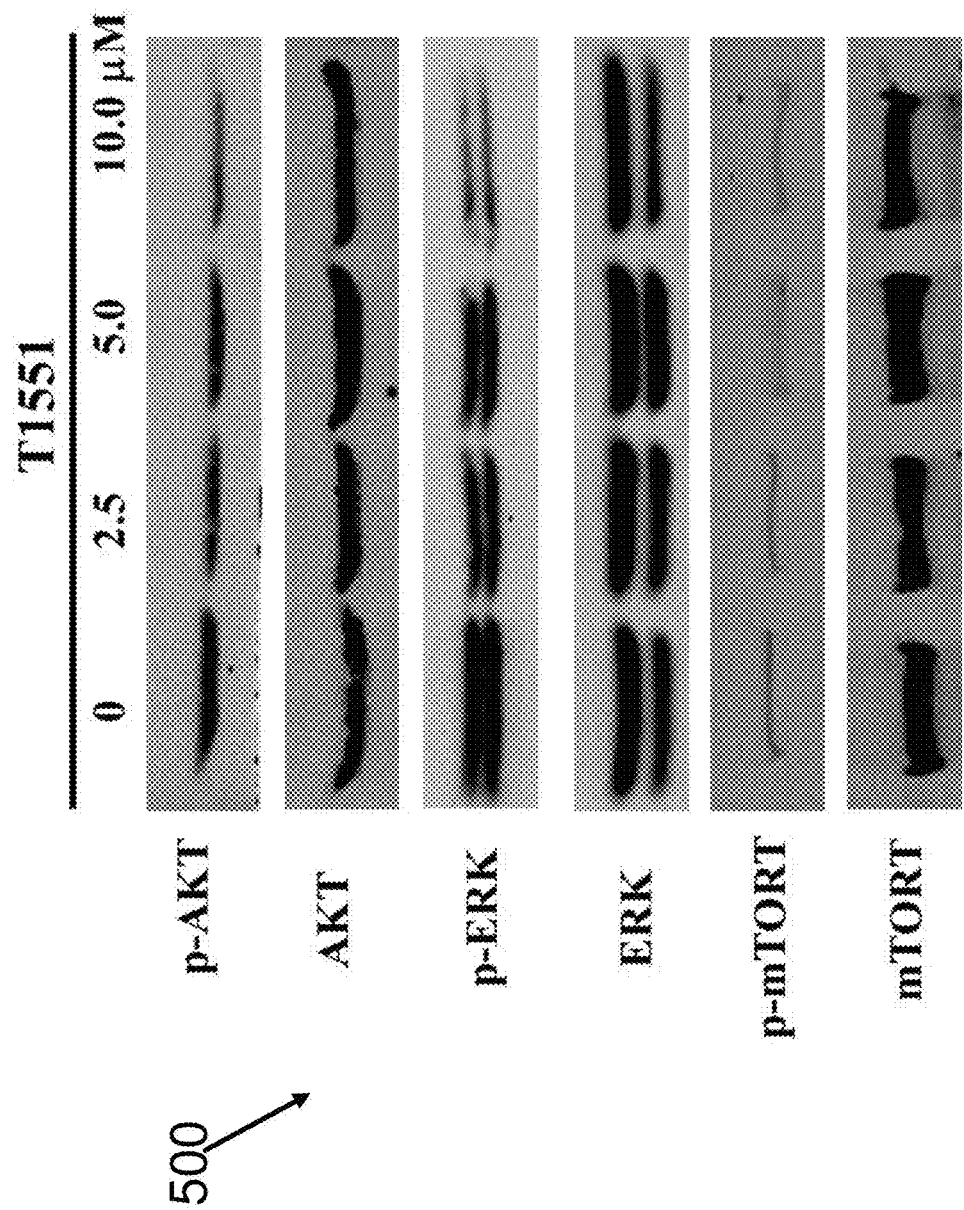
FIG. 5 shows the activation of PI3K/AKT/mTOR and ERK signaling in A549 cells treated with compound T1551 for 24 hr in accordance with an example embodiment.

Example 6 Effect of Compound T1551 in Suppressing the Activation of PI3K/AKT/mTOR and ERK Signaling in A549 Cells FIG. 5 shows the western blot analysis 500 for the expression of p-AKT, AKT, p-ERK, ERK, p-mTORT and mTORT in A549 cells treated with different concentrations of compound T1551 (i.e. 0, 2.5, 5 and 10 μM).

eIF4E is a key event downstream of ras and PI3K/AKT/mTOR signaling pathway, which is frequently activated in a diverse range of human cancers. FGFR3 is one of the receptors that promote cell survival by stimulating PI3K/AKT/mTOR signaling, and can also activate AKT and ERK13. The effect of compound T1551 in the regulation of the activation of AKT, ERK and mTOR through inhibiting PRMT5 was examined to further analyze the molecular mechanism underlying PRMT5-dependent regulation of FGFR3. As shown in FIG. 5, at the 10.0 μM of compound T1551, the protein levels of phosphorylated AKT, ERK and mTOR in A549 cells significantly decreased, indicating that compound T1551 was able to suppress the activation of PI3K/AKT/mTOR and ERK signaling mediated by PRMT5.

Example 7 Interaction Features of Compound T1551 with PRMT5

Figure 6A:
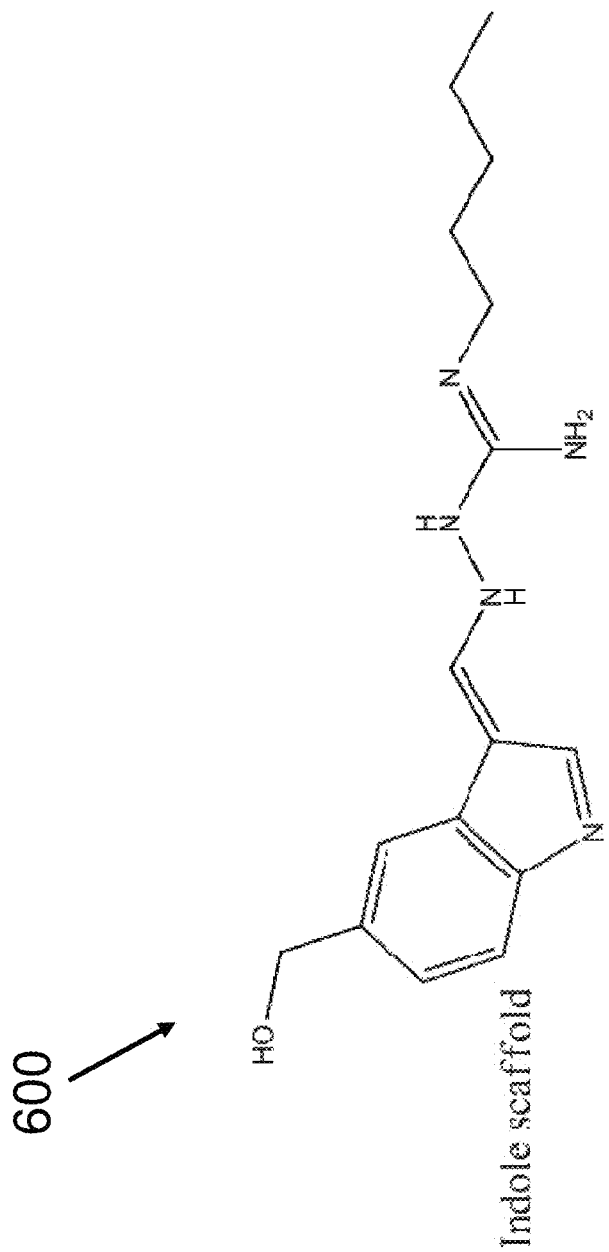
FIG. 6A shows the chemical structure of compound T1551 in accordance with an example embodiment. The blue structure represents the indole scaffold.

FIG. 6A shows the chemical structure 600 of compound T1551. Compound T1551 has an indole scaffold represented as a blue structure in FIG. 6A.

Figure 6B:
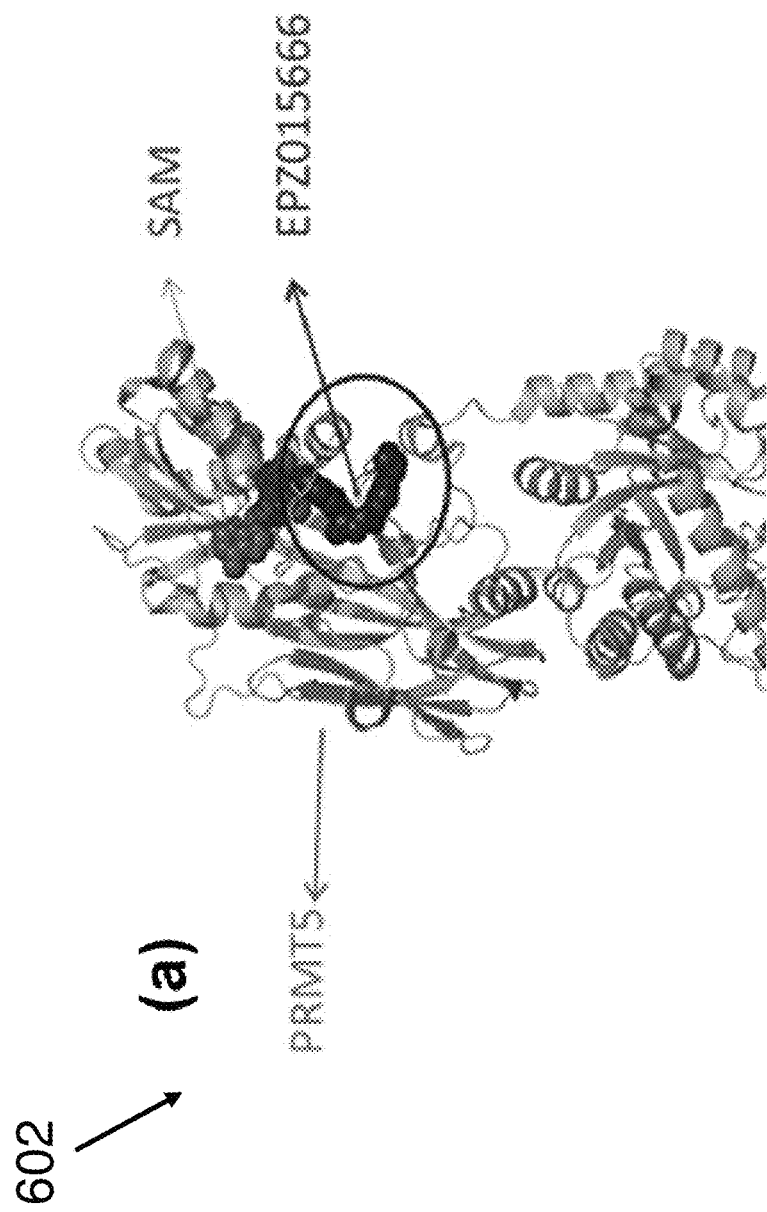
FIG. 6B shows a crystal structure of PRMT5-SAM-EPZ015666 (PDBID: 4x61) in accordance with an example embodiment
Figure 6C:
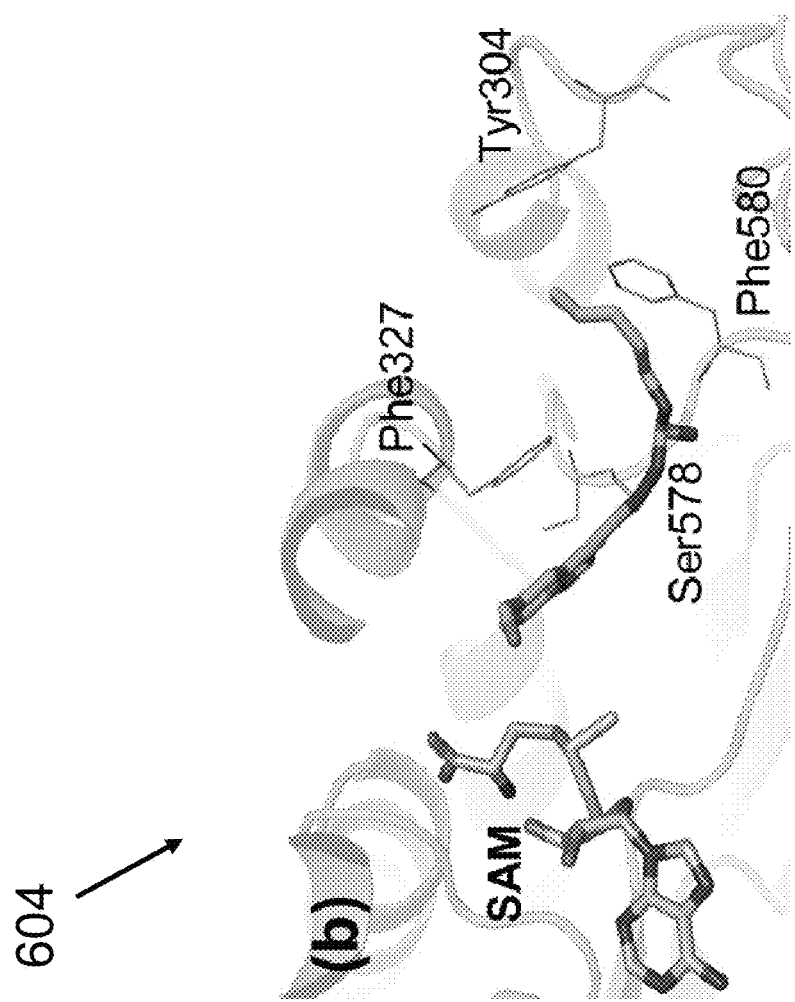
FIG. 6C shows the binding mode of PRMT5 with compound T1551 in accordance with an example embodiment.
Figure 6D:
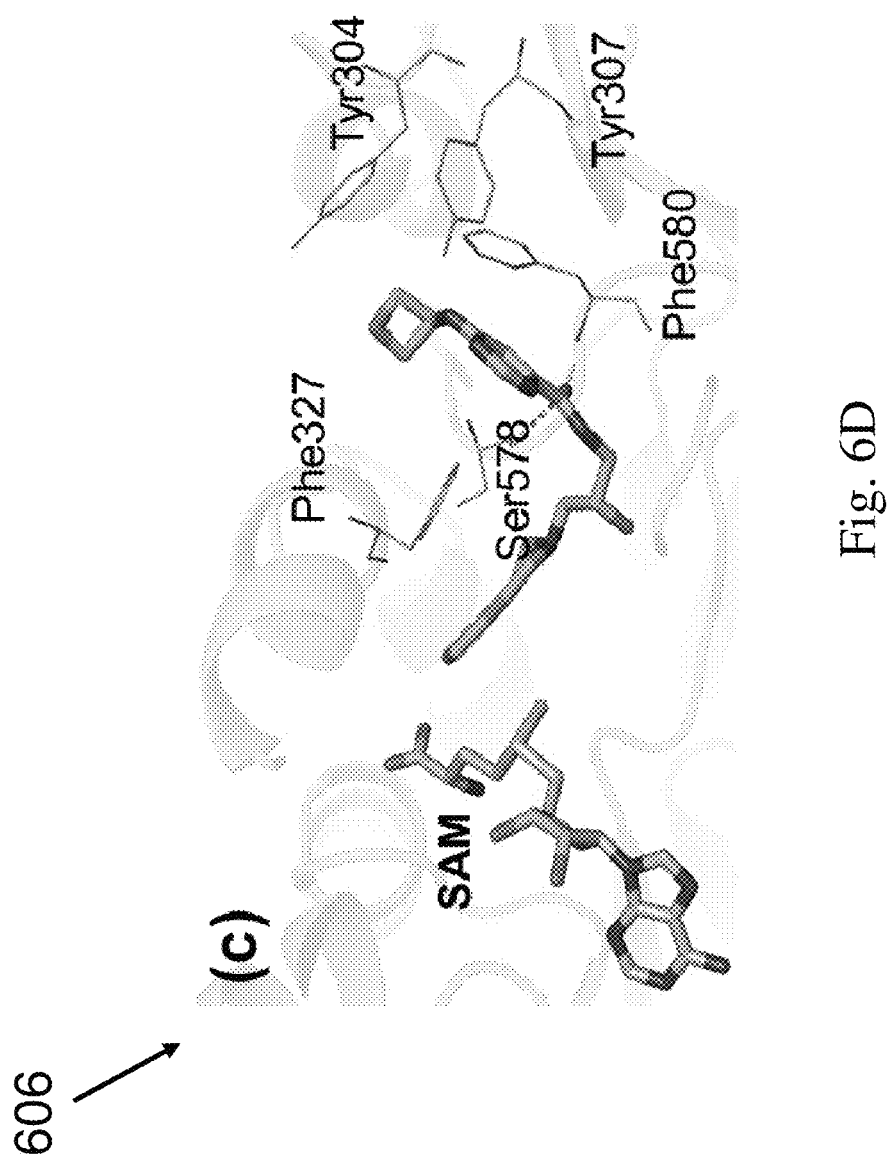
FIG. 6D shows the binding mode of PRMT5 with EPZ015666 in accordance with an example embodiment.

FIG. 6B shows a crystal structure 602 of PRMT5-SAM-EPZ015666. FIG. 6C is a drawing 604 showing the binding mode of PRMT5 with compound T1551. FIG. 6D is a drawing 606 showing the binding mode of PRMT5 with EPZ015666. Compound T1551 binds to PRMT5 protein with the glide gscore −9.33 kcal/mol. The interaction features of compound T1551 and co-crystalized EPZ015666 with PRMT5 were compared. The detailed binding mode was shown in FIGS. 6B-6D. Similar to EPZ015666, T1551 buried in a hydrophobic pocket composed of Tyr304, Phe327, Ser578 and Phe580 when interacting with PRMT5 as shown in FIG. 6C. The benzene ring of compound T1551 in indole scaffold formed strong cation-π interaction with the sulfur atom of SAM, as observed in PRMT5-EPZ015666 complex. In addition, compound T1551 also formed a hydrogen bond with the main-chain oxygen atom of Ser578, further fastening its interaction with PRMT5. The results confirm that the compound T1551 is an inhibitor of PRMT5.

FIGS. 1-6 shows that compound T1551 with the indole scaffold was identified as a PRMT5 inhibitor. Compound T1551 can not only decrease cellular viability and symmetric demethylation level of histone 4 in A549 cells, but also inhibit PRMT5 methyltransferase activity. Moreover, T1551 is able to downregulate the protein expression of oncogene FGFR3/eIF4E via inhibiting PRMT5, and then suppress the activation of PI3K/AKT/mTOR and ERK signaling. The key cation-π interaction between the benzene ring of compound T1551 and sulfur atom of SAM is responsible for its inhibitory activity against PRMT5. The identification of this inhibitor and functional biology study of PRMT5 contribute to the development of PRMT5 inhibitor for the treatment of cancer.

Figure 7:
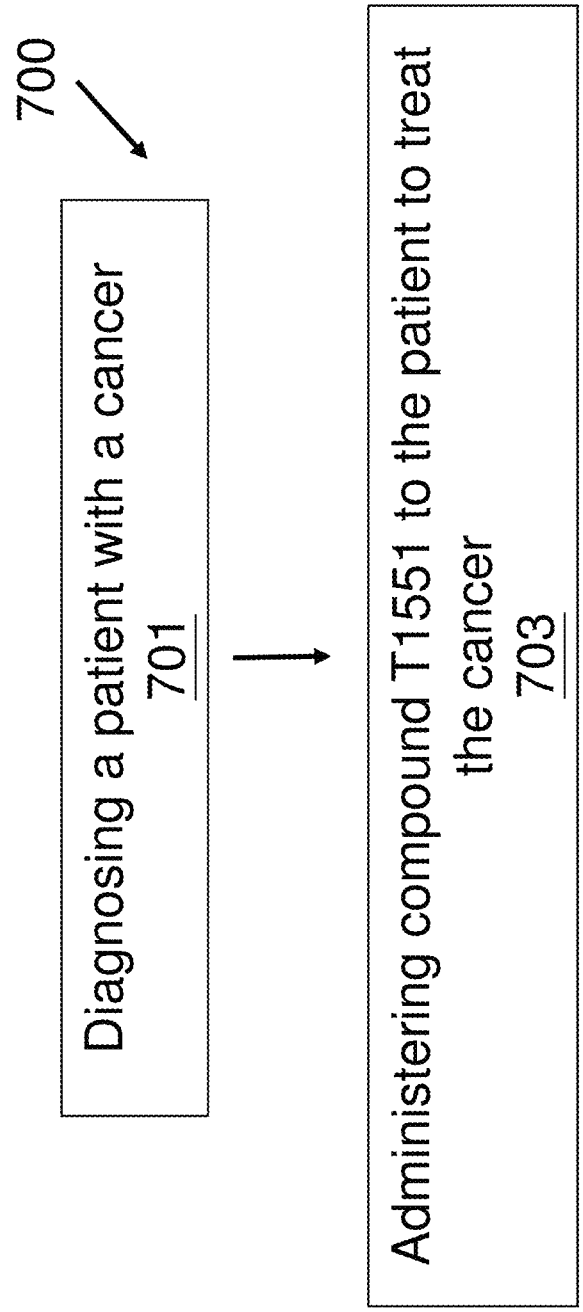
FIG. 7 shows a method of treating cancer in accordance with an example embodiment.

FIG. 7 shows a method 700 of treating cancer in a patient. Block 701 states diagnosing a patient with a cancer. In one example embodiment, a biological sample is obtained from a patient. Whether PRMT5 is overexpressed in the biological sample is detected by comparing a level of PRMT5 overexpression in the biological sample with a level of PRMT5 expression in a control group. If the level of the PRMT5 expression in the biological sample is higher than that in the control group, the patient is diagnosed as the patient with the cancer.

In one example embodiment, the biological sample is a tissue sample, a blood sample or a plasma sample from the patient. In one example embodiment, the biological sample is obtained by biopsies. In one example embodiment, the control group is a biological sample from a normal or healthy sample, cells or tissues. In one example embodiment, the control group is a biological sample from a normal or healthy person.

Block 703 states administering compound T1551 to the patient to treat the cancer.

In one example embodiment, the compound is administered directly or in the form of pharmaceutical compositions with suitable carriers or excipients. In one example embodiment, suitable routes of administration may, for example, include oral, rectal, transmucosal, nasal, or intestinal administration and parenteral delivery. The compound or the pharmaceutical composition that includes the compound can be administered locally. For example, the compound can be delivered via injection or in a targeted drug delivery system, such as a depot or sustained release formulation.

In one example embodiment, the cancer is the cancer associated with overexpression of PRMT5. In one example embodiment, the cancer is the cancer whose tumor cells express a higher level of PRMT5 than normal cells express. In one example embodiment, the cancer is lung cancer. In one example embodiment, the cancer is non-small cell lung cancer.

As used herein, the term "administration" or "administering" refers to providing a compound of an example embodiment and/or prodrugs thereof to a person in need of treatment.

As used herein, the term "disease associated with overexpression of PRMT5" refers to a disease that is associated with or characterized by a higher expression of PRMT5 compared with that of normal or healthy sample including cells or tissues.

As used herein, the term "normal cells" refers to the cells which do not exhibit uncontrolled cell growth and the ability to metastasize. The term "normal cells" also include but not limited to "benign cells", "non-cancer cells" and "non-malignant cells".

As used herein, the term "overexpress" or "overexpression" refers to increasing the expression of a protein to a level higher than normal cells or non-cancer cells produce.

As used herein, the term "patient" encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like.

As used herein, the term "PRMT5 inhibitor" refers to a therapeutic agent that can reduce or inhibit expression of PRMT5, or the activity of PRMT5, or the interaction between PRMT5 and histone.

As used herein, the term "pharmaceutically acceptable excipient" refers to pharmacologically inactive substances that are added to a pharmaceutical preparation in addition to the active pharmaceutical ingredient. Pharmaceutically acceptable excipients may take the function of vehicle, diluent, release, disintegration or dissolution modifying agent, absorption enhancer, stabilizer or a manufacturing aid among others.

As used herein, the term "therapeutically effective amount" refers to any amount of a compound which, as compared to a corresponding patient who has not received such amount, results in improved treatment, healing, prevention, or amelioration of a disease, disorder, or side effect, or a decrease in the rate of advancement of a disease or disorder.

As used herein, the term "treat," "treating" or "treatment" refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

What is claimed is:

1. A method of treating lung cancer in a patient, comprising:
administering a therapeutically effective amount of a compound to the patient to treat the lung cancer, wherein the compound is represented by Formula I,

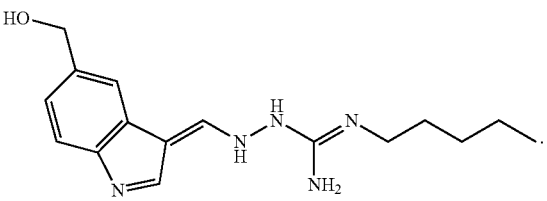

Formula I

2. The method of claim 1, wherein the lung cancer is non-small cell lung cancer.

3. The method of claim 1, wherein tumor cells of the lung cancer express a higher level of protein arginine methyltransferase 5 (PRMT5) than normal cells do.

4. The method of claim 2, wherein tumor cells of the non-small cell lung cancer express a higher level of PRMT5 than normal cells do.

5. The method of claim 1, wherein the compound is administered in combination with one or more PRMT5 inhibitors.

6. The method of claim 1 further comprising:
obtaining a biological sample from the patient;
detecting whether PRMT5 is overexpressed in the biological sample by comparing a level of PRMT5 expression in the biological sample with a level of PRMT5 expression in a control group; and
diagnosing the patient whose biological sample has higher level of the PRMT5 expression than that in the control group.

7. The method of claim 6, wherein the biological sample is a tissue sample, a blood sample or a plasma sample from the patient.

* * * * *